United States Patent [19]
Coufal et al.

[11] Patent Number: 5,571,106
[45] Date of Patent: Nov. 5, 1996

[54] SURGICAL CUTTING INSTRUMENT

[75] Inventors: Hans J. Coufal; Robert K. Grygier, both of San Jose, Calif.

[73] Assignee: International Business Machines Corporation, Armonk, N.Y.

[21] Appl. No.: 442,905

[22] Filed: May 17, 1995

[51] Int. Cl.$^6$ ............................ A61B 17/56; A61B 17/16
[52] U.S. Cl. ............................... 606/80; 606/79; 606/180
[58] Field of Search ................................ 606/79, 80, 81, 606/82, 83, 84, 85, 180; 408/204, 205

[56] References Cited

U.S. PATENT DOCUMENTS

| | | | |
|---|---|---|---|
| 2,714,318 | 8/1955 | Norman et al. | 408/204 |
| 3,037,264 | 6/1962 | Mossberg | 29/106 |
| 3,412,733 | 11/1968 | Ross . | |
| 3,702,611 | 11/1972 | Fishbein . | |
| 3,732,858 | 5/1973 | Banko . | |
| 3,775,819 | 12/1973 | Ribich | 29/103 A |
| 3,811,163 | 5/1974 | Frederick et al. | 29/103 A |
| 4,273,117 | 6/1981 | Neuhauser . | |
| 5,084,052 | 1/1992 | Jacobs | 606/79 |
| 5,190,548 | 3/1993 | Davis | 606/80 |
| 5,203,653 | 4/1993 | Kudla | 408/207 |
| 5,366,468 | 11/1994 | Fucci et al. | 606/180 |
| 5,405,348 | 4/1995 | Anspach, Jr. et al. | 606/180 |

FOREIGN PATENT DOCUMENTS

| | | |
|---|---|---|
| 2759231 | 7/1979 | Germany . |
| 2830566 | 1/1980 | Germany . |
| 1553078A | 3/1990 | U.S.S.R. . |

OTHER PUBLICATIONS

Roberts et al., "Manufacturing Processes", Manufacturing Engineering Technology, Norwalk State Technical College, Norwalk, Connecticut.

Primary Examiner—Michael Powell Buiz
Assistant Examiner—Scott B. Markow
Attorney, Agent, or Firm—Robert B. Martin

[57] ABSTRACT

The present invention relates to an improved high speed rotary bone cutter comprising a drive shaft and a cutting head. The drive shaft has an elongated housing rotably mounted on the shaft. The housing has an enclosed fluid passageway around the shaft for the flow of cutting fluid. The passageway insulates the flowing fluid from the high rotational speed of the drive shaft.

3 Claims, 1 Drawing Sheet

SURGICAL CUTTING INSTRUMENT

FIELD OF THE INVENTION

The invention generally relates to surgical cutting instruments and more particularly high speed orthopedic bone cutter.

BACKGROUND OF THE INVENTION

Modern surgical procedures increasingly involve the cutting of bone material. For example, joint replacement surgery such as hip replacement involves the hollowing out of the interior of the femur to provide a cavity to accommodate an artificial implant.

It is known in the art that the heating of the bone during the cutting process should be minimized to avoid medical complications such as bone necrosis. Preferably, the temperature at the bone interface should not exceed about 50° C. for more than 1 second. This is accomplished by minimizing heat generation during the bone cutting process and by maximizing heat removal from the cutting area. Heat is generally removed from the cutting area by a cutting fluid (e.g. saline solution) which functions as a heat sink and also removes bone chips from the cutting area.

U.S. Pat. No. 5,190,548 discloses a surgical bone reamer having a central bore in the shank of the reamer for carrying cutting fluid. The fluid exits the bore at the cutting head of the reamer and flows along the annular passageway between the shank and the bore hole. Unfortunately, at high speeds (e.g. greater than 40,000 to 50,000 rpm) centrifugal force will prevent the flow of cutting fluid through the central bore of the drill, thereby inhibiting cooling of the bone surface during the drilling process.

It is an object of the present invention to provide a high speed rotary bone cutter which reduces heat generation at the cutting surface and enhances heat removal from the cutting area. Other objects and advantages will be apparent from the following disclosure.

SUMMARY OF THE INVENTION

The present invention relates to an improved high speed rotary bone cutter comprising a drive shaft and a cutting head. The drive shaft has an elongated housing rotably mounted on the shaft. The housing has an enclosed fluid passageway around the shaft for the flow of cutting fluid. The cutting head is attached at one end of the drive shaft. The cutting head comprises a plurality of blades radially mounted on the head. Each blade has a cutting edge which is perpendicular to the rotational axis of the drive shaft. The cutting head also has a plurality of fluid channels which direct cutting fluid from the passageway to each of the cutting edges. Preferably, each of the cutting edges has a positive rake angle.

A more thorough disclosure of the present invention is presented in the detailed description which follows in from the accompanying FIGURE.

DETAILED DESCRIPTION OF THE INVENTION

Figure 1:
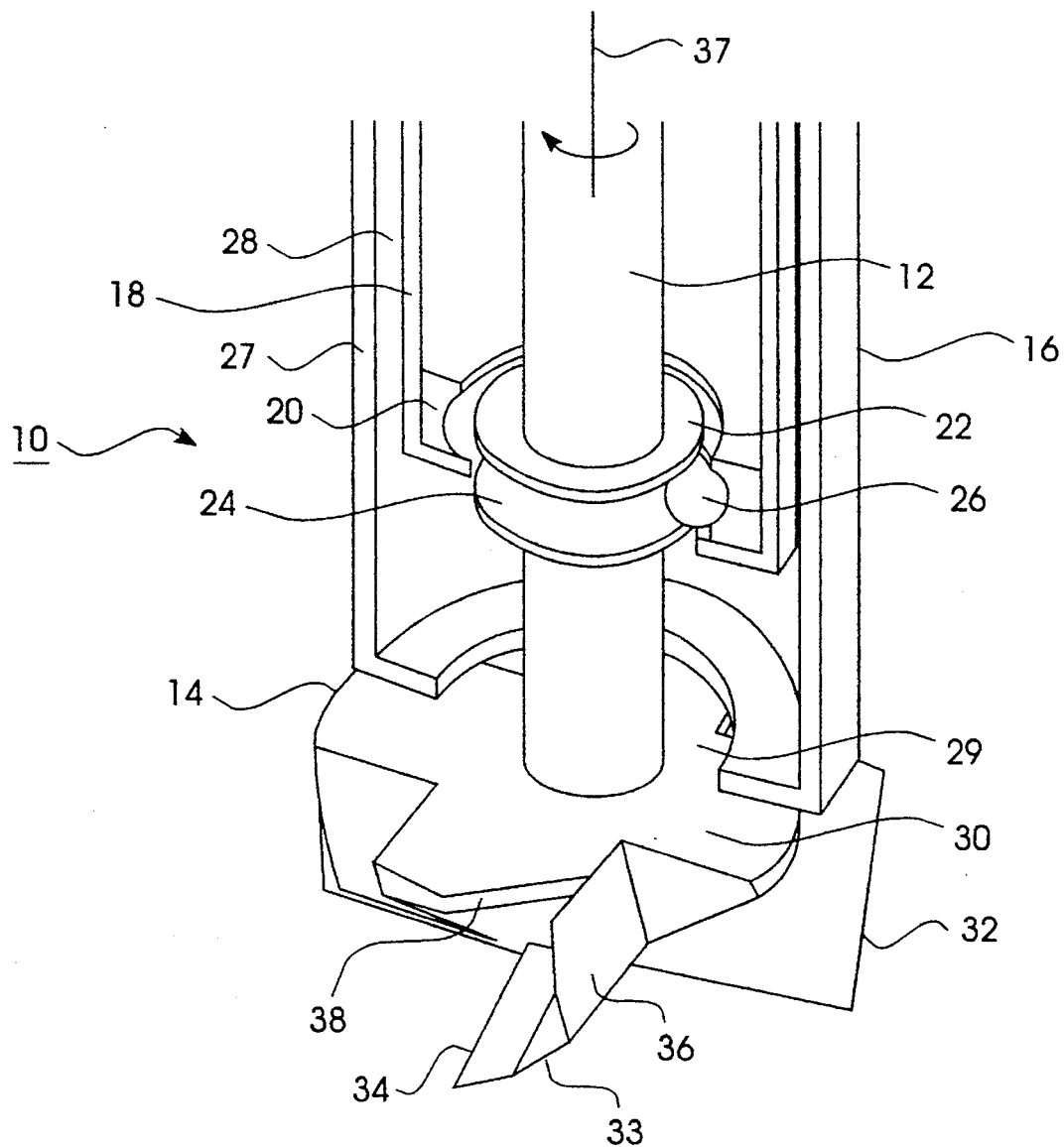
FIG. 1 is a sectional view of the rotary bone cutter.

The present invention relates to an improved high speed rotary bone cutter. Referring to FIG. 1, the bone cutter 10 comprises drive shaft 12 and cutting head 14. The drive shaft 12 has housing 16 rotably mounted on the shaft. The housing provided with an inner core 18 having a plurality of races (outer race 20 shown at the end of the core). The inner core 18 is rigidly fixed to housing 16. Drive shaft 12 is provided with a plurality of collars (collar 22 shown) having a plurality of races (inner race 24 shown). Housing 16 is positioned on the drive shaft 12 to align outer race 20 with inner race 24 for receipt of bearings 26. An enclosed annular fluid passageway 28 is formed around the drive shaft between the wall of inner core 18 and outer wall 27 of housing 16. The wall of inner core 18 separates the passageway from the rotation of shaft 12. The end of housing 16 is provided with an opening 29 to direct fluid flow out of the housing onto the top surface 30 of cutting head 14. Cutting head 14 is provided with a plurality of radially mounted cutting blades 32. Referring to blade 33, each cutting blade comprises cutting edge 34 and channel 36. Cutting edge 34 preferably has a positive axial rake angle and extends outwardly from and perpendicular to the rotational axis 37 of drive shaft 12. The cutting edge 38 may also have a positive radial rake angle. Channel 36 is preferably located on the back side of blade 33 and functions to direct cutting fluid flowing out from annular fluid passageway 29 to the front portion of the cutting edge of blade 32 which is positioned radially behind blade 33. In an alternative embodiment, the channel 36 can comprise a plurality of bores through top surface 30 of the drilling head 14 positioned to direct fluid flow from annular fluid passageway 29 to a cutting edge of each of the cutting blades.

In operation, the cutter is rotated at high speeds of about 70,000 to about 100,000 rpm. Cutting fluid is flowed by pump through inlet (not shown) in housing 16 into fluid passageway 28. Inner core 18 insulates the cutting fluid flowing in passageway 28 from the high rotation speed of drive shaft 12 as it flows along the length of housing 16. The cutting fluid exits the housing through annular opening 29 at the end of the housing and flows onto the top surface 30 of cutting head 14. The fluid then flows into channel 36 which directs it towards the cutting edge of each of the cutting blades. Because the fluid flow is directed in the area directly in front of the cutting edge, hot bone chips are immediately cooled and removed from the surface of the bone to minimize any heat transfer between the bone chips and the surface of the bone. The bone chips move up along the front side of the cutting blade past notch 38 in surface 30 and away from the cutting site.

In an alternative embodiment, the housing 16 of cutter 10 may be provided with an outer annular core (not shown) which would function to evacuate the mixture of cutting fluid and bone chips from the cutting site. The outer core would extend along the housing to the cutting head.

Although this invention has been described with respect to specific embodiments, details thereof are not to be construed as limitations for it will be apparent that various embodiments, changes and modifications may be resorted to without departing from the spirit and scope thereof, and it is understood that such equivalent embodiments are intended to be included within the scope of this invention.

We claim:

1. A high speed rotary bone cutter comprising:
   (a) an elongated housing having a proximal end and a distal end, said housing comprising an inner tube surrounded by a outer tube to define a space between said inner tube and said outer tube, said space defining an enclosed fluid passage and said outer tube being open at its distal end;
   (b) a drive shaft having a proximal end and a distal end, the drive shaft rotatably mounted inside of said inner tube, said distal end projecting distally beyond said distal end of said inner tube and said distal end of said outer tube, the inner tube separating the fluid passage from the rotation of the drive shaft;

(c) a cutting head attached to the distal end of the drive shaft and comprising (i) a plurality of blades radially mounted on the head, each blade having a cutting edge extending outwardly and perpendicular to a rotational axis of the drive shaft, and (ii) a plurality of fluid channels to direct cutting fluid that exits from the open distal end of the outer tube to each of the cutting edges.

2. The bone cutter of claim 1 wherein the plurality of channels are formed on the back sides of plurality of blades.

3. The bone cutter of claim 1 wherein the shaft and inner core each have races which are aligned for receipt of bearings.

* * * * *